United States Patent
Kawashima et al.

(10) Patent No.: US 7,855,199 B2
(45) Date of Patent: Dec. 21, 2010

(54) HETEROCYCLIC COMPOUND AND ANTI-MALIGNANT-TUMOR AGENT CONTAINING THE SAME AS ACTIVE INGREDIENT

(75) Inventors: Seiichiro Kawashima, Saitama-ken (JP); Mitsuko Kawashima, legal representative, Saitama-ken (JP); Hiroto Kawashima, legal representative, Shizuoka-ken (JP); Masato Kawashima, legal representative, Hiroshima-ken (JP); Toshiyuki Matsuno, Tokyo (JP); Shinichi Yaguchi, Tokyo (JP); Yoshio Tsuchida, Tokyo (JP); Kenichi Saitoh, Tokyo (JP); Tetsuo Watanabe, Tokyo (JP)

(73) Assignee: Zenyaku Kogyo Kabushiki Kaisha, Tokyo (JP)

( * ) Notice: Subject to any disclaimer, the term of this patent is extended or adjusted under 35 U.S.C. 154(b) by 963 days.

(21) Appl. No.: 10/594,994

(22) PCT Filed: Mar. 30, 2005

(86) PCT No.: PCT/JP2005/006111

§ 371 (c)(1),
(2), (4) Date: Jan. 17, 2007

(87) PCT Pub. No.: WO2005/095389

PCT Pub. Date: Oct. 13, 2005

(65) Prior Publication Data

US 2008/0287431 A1    Nov. 20, 2008

(30) Foreign Application Priority Data

Mar. 31, 2004 (JP) .............................. 2004-103273

(51) Int. Cl.
| | |
|---|---|
| *A61K 31/4184* | (2006.01) |
| *A61K 31/506* | (2006.01) |
| *A61K 31/53* | (2006.01) |
| *A61K 31/5377* | (2006.01) |
| *C07D 413/14* | (2006.01) |
| *C07D 235/10* | (2006.01) |
| *C07D 251/18* | (2006.01) |
| *C07D 265/30* | (2006.01) |

(52) U.S. Cl. .................. 514/232.2; 514/232.5; 544/82; 544/83

(58) Field of Classification Search ................ None
See application file for complete search history.

(56) References Cited

U.S. PATENT DOCUMENTS

| | | |
|---|---|---|
| 6,251,900 B1 | 6/2001 | Kawashima et al. |
| 7,071,189 B2 | 7/2006 | Kawashima et al. |
| 2006/0009440 A1 | 1/2006 | Kawashima et al. |
| 2006/0247232 A1 | 11/2006 | Kawashima et al. |

FOREIGN PATENT DOCUMENTS

| | | |
|---|---|---|
| WO | 96 10024 | 4/1996 |
| WO | 02 088112 | 11/2002 |
| WO | 2004 032930 | 4/2004 |

OTHER PUBLICATIONS

Voskoglou-Nomikos, et al., Clin. Can. Res. vol. 9, pp. 4227-4239 (2003).*
U.S. Appl. No. 11/847,593, filed Aug. 30, 2007, Haruta, et al.
U.S. Appl. No. 11/404,078, filed Apr. 14, 2006, Yaguchi, et al.

* cited by examiner

*Primary Examiner*—Kamal A Saeed
*Assistant Examiner*—Michael Barker
(74) *Attorney, Agent, or Firm*—Oblon, Spivak, McClelland, Maier & Neustadt, L.L.P.

(57) ABSTRACT

Heterocyclic compounds represented by the formula I and anti-malignant-tumor agents containing the heterocyclic compounds as effective components:

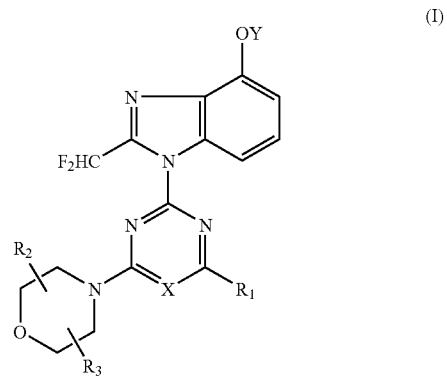

(I)

wherein X represents nitrogen atom or CH; Y represents $C_1$-$C_6$ alkyl; $R_1$ represents morpholino (which may be substituted with one to four $C_1$-$C_6$ alkyl); and $R_2$ and $R_3$ each represent hydrogen atom or $C_1$-$C_6$ alkyl.

18 Claims, No Drawings

HETEROCYCLIC COMPOUND AND ANTI-MALIGNANT-TUMOR AGENT CONTAINING THE SAME AS ACTIVE INGREDIENT

TECHNICAL FIELD

The present invention relates to heterocyclic compounds represented by the formula I and anti-malignant-tumor agents comprising the heterocyclic compounds as effective components:

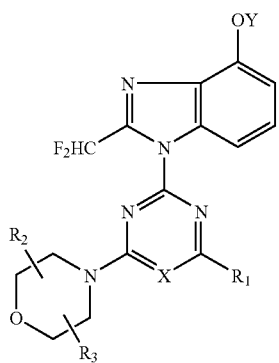

wherein X represents nitrogen atom or CH; Y represents $C_1$-$C_6$ alkyl; $R_1$ represents morpholino (which may be substituted with one to four $C_1$-$C_6$ alkyl); and $R_2$ and $R_3$ each represent hydrogen atom or $C_1$-$C_6$ alkyl.

BACKGROUND ART s-Triazine (1,3,5-triazine) and pyrimidine derivatives have been researched in the fields of synthetic resins, synthetic fibers, dyes and agricultural chemicals and a great number of such compounds have been synthesized. In the field of pharmaceuticals, researches have been made with respect to antitumor, anti-inflammatory, analgesic and antispasmodic activities. Especially, hexamethylmelamine (HMM) is well-known which has been developed as analogue of anti-malignant-tumor agent triethylenemelamine (TEM) (see, for example, non-patent reference 1).

TEM is known as alkylating agent and is s-triazine derivative having cytotoxic antitumor activity. HMM has been marketed in Europe under the indications for the treatment of ovarian and small cell lung cancers, and its action on solid cancers have attractive.

Among the s-triazine derivatives, imidazolyl-s-triazine derivatives which exhibit cytotoxic and selective aromatase inhibitory activities have been proposed as medicine for estrogen-dependent diseases such as endometriosis, multicystic ovarium, mastopathy, endometrium carcinoma and breast cancer (see, for example, patent reference 1).

In order to expand antitumor activities of HMM and to decrease aromatase inhibitory activities of imidazolyl-s-triazine derivatives, we, the inventors, studied to find s-triazine and pyrimidine derivatives with substitution of benzimidazole ring for imidazole ring (see, for example, patent references 2 and 3).

We developed the studies for further enhancement of the antitumor activities in these compounds to find s-triazine and pyrimidine derivatives with specific substituents at position 2 of benzimidazole ring (see, for example, patent reference 4).

non-patent reference 1: B. L. Johnson et al. Cancer, 42: 2157-2161 (1978)
patent reference 1: WO93/17009
patent reference 2: WO99/05138
patent reference 3: WO00/43385
patent reference 4: WO02/088112

SUMMARY OF THE INVENTION

Problems to be Solved by the Invention

However, in non-patent reference 1, there is still room for improvement on HMM with respect to its antitumor spectrum and intensity of antitumor activities against solid cancers. As to imidazolyl-s-triazine derivatives in patent reference 1, they are limitative in application since they exhibit considerably higher aromatase inhibitory activities than their cytotoxic activities and application of them to cancerous patients other than those who suffer from estrogen-dependent diseases may lead to development of secondary effects such as menstrual disorders due to lack of estrogen. There are still, therefore, strong demands on medicines with no aromatase inhibitory activities and effective for solid cancers.

In the compounds shown in patent references 2 and 3, aromatase inhibitory activities are relieved by substituting benzimidazole ring for the imidazole ring; however, there is still room for improvement with respect to their antitumor activities. In the compounds shown in patent reference 4, their in vitro antitumor activities are excellent since they have specific substituents at position 2 of benzimidazole ring; however, the compounds further having hydroxyl at benzimidazole ring have insufficient pharmacokinetics and cannot attain sufficient antitumor effects through oral administration.

Means or Measures for Solving the Problems

We, the inventors, further developed the studies to find out that heterocyclic compounds represented by the formula I having $C_1$-$C_6$ alkoxy at position 4 of benzimidazole ring have remarkable improvement in pharmacokinetics and excellent antitumor activities, thus completing the present invention.

The terms used for definition of letters in the formula I, by which the heterocyclic compounds of the present invention are represented, will be defined and exemplified in the following.

The term "$C_1$-$C_6$" refers to a group having 1 to 6 carbon atoms unless otherwise indicated.

The term "$C_1$-$C_6$ alkyl" refers to a straight- or branched-chain alkyl group such as methyl, ethyl, n-propyl, isopropyl, n-butyl, tert-butyl, n-pentyl or n-hexyl.

The compounds according to the present invention may be as follows, though the present invention is not limited to these compounds.

2-(2-difluoromethyl-4-methoxybenzimidazol-1-yl)-4-(3,3-dimethylmorpholino)-6-morpholino-1,3,5-triazine 2-(2-difluoromethyl-4-methoxybenzimidazol-1-yl)-4-(cis-2,6-dimethylmorpholino)-6-morpholino-1,3,5-triazine 2-(2-difluoromethyl-4-methoxybenzimidazol-1-yl)-4-(trans-2,6-dimethylmorpholino)-6-morpholino-1,3,5-triazine 2-(2-difluoromethyl-4-methoxybenzimidazol-1-yl)-4-(2,2,5,5-tetramethylmorpholino)-6-morpholino-1,3,5-triazine 2-(2-difluoromethyl-4-methoxybenzimidazol-1-yl)-4,6-dimorpholino-1,3,5-triazine 2-(2-difluoromethyl-4-ethoxybenzimidazol-1-yl)-4,6-dimorpholino-1,3,5-triazine 2-(2-difluoromethyl-4-methoxybenzimidazol-1-yl)-4-(2,2-dimethylmorpholino)-6-morpholinopyrimidine
2-(2-difluoromethyl-4-methoxybenzimidazol-1-yl)-4,6-bis(2,2-dimethylmorpholino)pyrimidine
2-(2-difluoromethyl-4-methoxybenzimidazol-1-yl)-4-(cis-2,6-dimethylmorpholino)-6-morpholinopyrimidine
2-(2-difluoromethyl-4-methoxybenzimidazol-1-yl)-4-(trans-2,6-dimethylmorpholino)-6-morpholinopyrimidine
2-(2-difluoromethyl-4-methoxybenzimidazol-1-yl)-4,6-bis(cis-2,6-dimethylmorpholino)pyrimidine
2-(2-difluoromethyl-4-methoxybenzimidazol-1-yl)-4,6-dimorpholinopyrimidine
2-(2-difluoromethyl-4-methoxybenzimidazol-1-yl)-4-(cis-2,3-dimethylmorpholino)-6-morpholinopyrimidine
2-(2-difluoromethyl-4-methoxybenzimidazol-1-yl)-4-(2,2,5,5-tetramethylmorpholino)-6-morpholinopyrimidine
2-(2-difluoromethyl-4-ethoxybenzimidazol-1-yl)-4,6-dimorpholinopyrimidine
2-(2-difluoromethyl-4-ethoxybenzimidazol-1-yl)-4-(cis-2,3-dimethylmorpholino)-6-morpholinopyrimidine
2-(2-difluoromethyl-4-ethoxybenzimidazol-1-yl)-4-(2,2-dimethylmorpholino)-6-morpholinopyrimidine Especially preferable as the compounds of the present invention are compounds of the formula I with methoxy as substituents at position 4 of benzimidazole ring.

The compounds of the present invention may have asymmetric carbon atoms in the structure. It is to be understood that isomers due to such asymmetric carbon atom or mixture of any of the isomers are included in the category of the compounds according to the present invention.

Production Processes

The compounds of the present invention represented by the formula I may be prepared by, as shown in the following reaction formula, reacting cyanuric chloride or 2,4,6-trichloropyrimidine (compound II) as starting material with benzimidazole compound (compound V), morpholine compound (compound VI) and $R_1H$ (compound VII) successively in the order named.

Reaction Formula

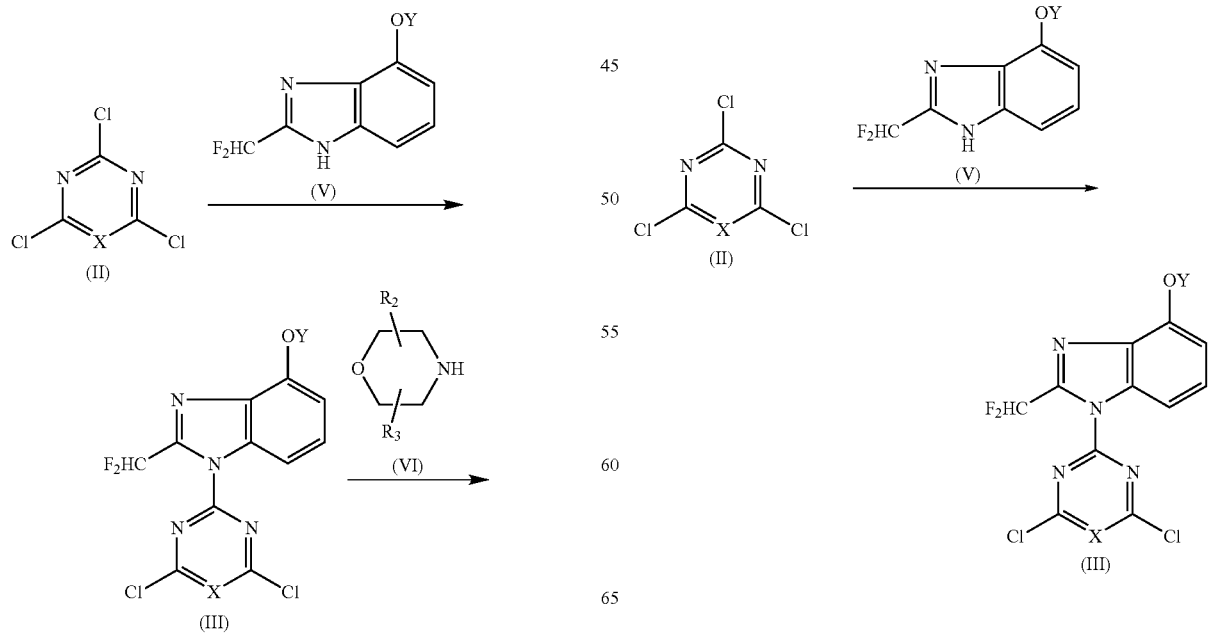

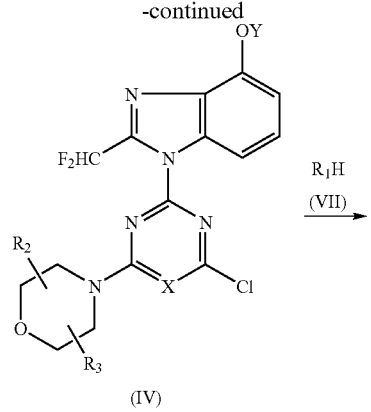

wherein $R_1$, $R_2$, $R_3$, X and Y are as defined above.

Next, the respective production processes will be described.

1) Production Process (i) of Intermediate III:

reaction formula (i)

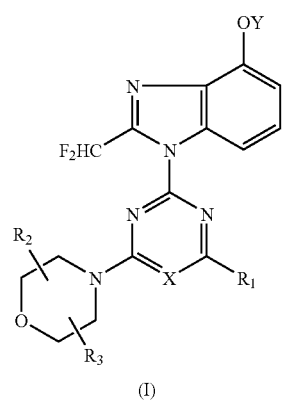

wherein X and Y are as defined above.

In a solvent, cyanuric chloride or 2,4,6-trichloropyrimidine (compound II) is reacted with benzimidazole compound (compound V) in the presence of hydrogen chloride trapping agent to obtain the intermediate III.

The hydrogen chloride trapping agent used in this reaction may be, for example, sodium hydroxide, potassium hydroxide, sodium carbonate, potassium carbonate, triethylamine or pyridine. The solvent used may be, for example, acetone, toluene, hexane, xylene, dioxane, tetrahydrofuran or dichloroethane or N,N-dimethylformamide (DMF).

In this reaction, 0.5-1.2 moles of the compound V is used per mole of the compound II in the presence of 0.5-2 moles of the hydrogen chloride trapping agent. The reaction is made at the temperature of −15° C.-5° C. for 0.5-2 hours, and further at the room temperature for 2-50 hours.

It is to be noted that the compound V may be also used as the hydrogen chloride trapping agent.

2) Production Process (ii) of Intermediate IV

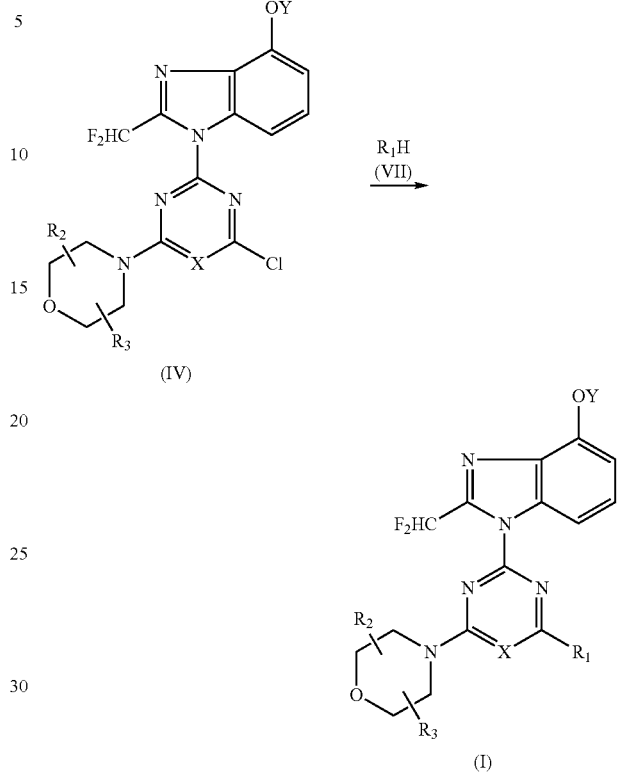

wherein $R_2$, $R_3$, X and Y are as defined above.

In the solvent, the intermediate III obtained in the above-mentioned production process (i) is reacted with morpholine compound (compound VI) in the presence of hydrogen chloride trapping agent to obtain the intermediate IV. The hydrogen chloride trapping agent used in this reaction may be the same as those in the above-mentioned production process (i). The solvent used may be DMF, acetone, toluene, xylene, dichloroethane or dichloromethane.

In this reaction, 1-10 moles of the compound VI is used per mole of the intermediate III and in the presence of 1-10 moles of the hydrogen chloride trapping agent. The reaction is made at the temperature of −5° C.-0° C. for 0.5-20 hours, and further at the temperature between room temperature and reflux flow temperature for 0.5-5 hours.

It is to be noted that the compound VI may be also used as the hydrogen chloride trapping agent.

3) Production Process (iii) of the Compound I

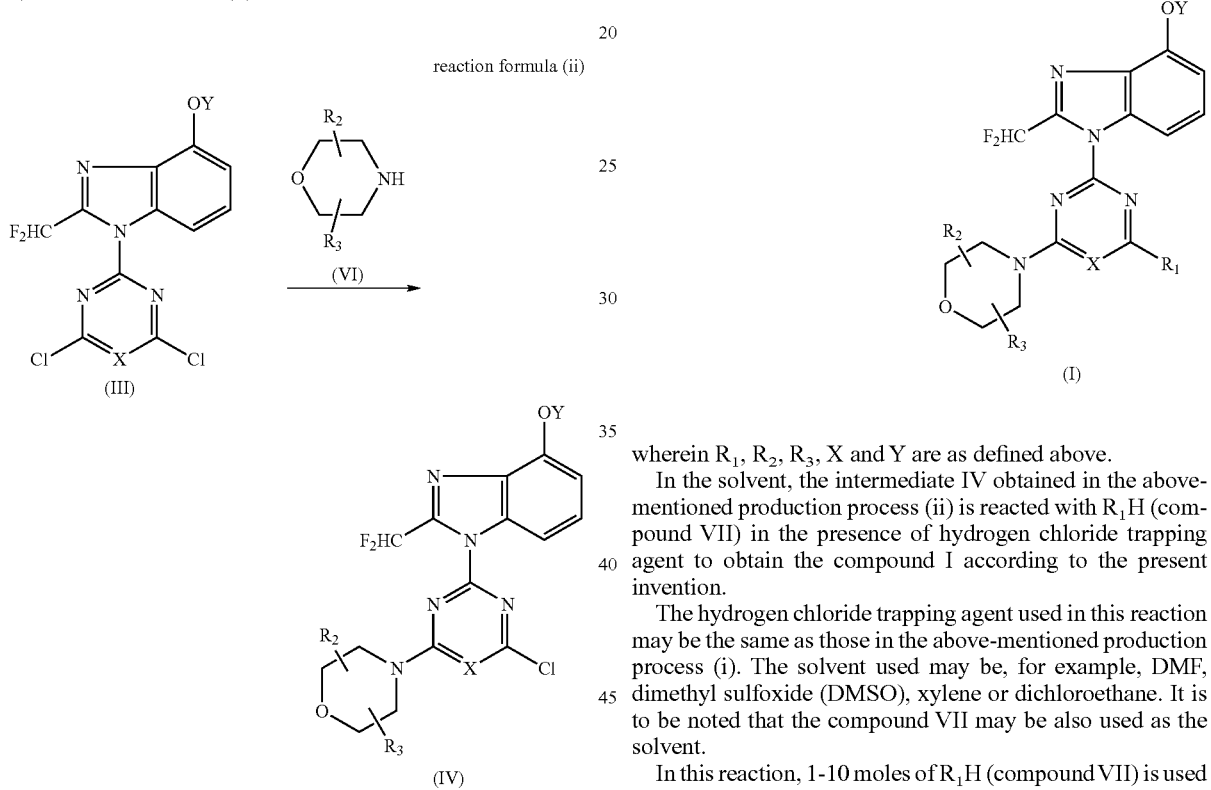

wherein $R_1$, $R_2$, $R_3$, X and Y are as defined above.

In the solvent, the intermediate IV obtained in the above-mentioned production process (ii) is reacted with $R_1H$ (compound VII) in the presence of hydrogen chloride trapping agent to obtain the compound I according to the present invention.

The hydrogen chloride trapping agent used in this reaction may be the same as those in the above-mentioned production process (i). The solvent used may be, for example, DMF, dimethyl sulfoxide (DMSO), xylene or dichloroethane. It is to be noted that the compound VII may be also used as the solvent.

In this reaction, 1-10 moles of $R_1H$ (compound VII) is used per mole of the intermediate IV at the temperature between the room temperature and 140° C. for 0.1-16 hours. In the case of the reaction in the presence of the hydrogen chloride trapping agent, 1-10 moles of the hydrogen chloride trapping agent is used per mole of the intermediate IV. It is to be noted that the compound VII may be also used as the hydrogen chloride trapping agent.

In such production of the compound I and when the compounds VI and VII are the same, the production processes (ii) and (iii) may be carried out in a single step to obtain the compound I. In this case, the reaction conditions are as mentioned in the above with respect to the production process (ii) except that 2-10 moles of the compound VI or VII is used per mole of the compound III and that the reaction is made at the temperature of −10° C.-5° C. for 0.1-5 hours, and further at the temperature between room temperature and 120° C. for 3-50 hours.

When the compound V, VI or VII used in the production process (i), (ii) or (iii) has lower reactivity, it is preferable that each production process is carried out after treatment with sodium hydride. In the case of sodium hydride being used, 1.0-1.2 moles of sodium hydride is used per mole of the starting material in the production process (compound II, III or IV).

The above-mentioned production processes (i), (ii) and (iii) may be carried out in any exchanged order. In such a case, the reaction conditions may be varied to the extent that is obvious to a person having ordinary skill in the art.

The resultant products in the above-mentioned respective production processes may be separated and purified, as needs demand, by ordinary method such as extraction, concentration, neutralization, filtration, re-crystallization or column chromatography.

Next, pharmacokinetics and antitumor activities of the compound I of the present invention will be described. Numbers of the tested compounds in the tests 1 and 2 correspond to those in Examples referred to hereinafter.

Used as comparative compounds are the following compounds with hydroxyl at position 4 of benzimidazole ring which are included in the claim scope of the above-mentioned patent reference 4 and which comes nearest to the present invention.

Compound A: 2-(2-difluoromethyl-4-hydroxybenzimidazol-1-yl)-4-(cis-2,6-dimethylmorpholino)-6-morpholinopyrimidine Compound B: 2-(2-difluoromethyl-4-hydroxybenzimidazol-1-yl)-4-(2,2-dimethylmorpholino)-6-morpholinopyrimidine Compound C: 2-(2-difluoromethyl-4-hydroxybenzimidazol-1-yl)-4-(cis-2,3-dimethylmorpholino)-6-morpholinopyrimidine Compound D: 2-(2-difluoromethyl-4-hydroxybenzimidazol-1-yl)-4-(trans-2,6-dimethylmorpholino)-6-morpholinopyrimidine Test 1 (Pharmacokinetics Study)

Pharmacokinetics study was conducted, using six-week-old BDF1 male mice. Test compound was dissolved in dichloromethane together with hydroxypropyl cellulose (low-molecular weight)(HPC(L)) 2.5 times as much as the drug weight, dried under reduced pressure and was suspended in distilled water so as to have the drug concentration of 20 mg/mL. The test compound was forcedly orally administered to mice fasting for 16 hours with dose of 200 mg/kg. One, two, four, eight and 24 hours after the administration, blood was collected from orbit of two mice to obtain serum 100 μL of the obtained serum was added with internal standard solution and 1 mL of distilled water and then test compound and internal standard substance were extracted from the resulting mixture by diethyl ether. The organic layers were evaporated to dryness under reduced pressure and residues were dissolved in eluent to obtain HPLC measurement sample. The analysis was performed by HPLC with reversed-phase column and the eluent used was acetonitrile-phosphate buffer (pH 2.5). The drug concentration in the test serum was calculated by the calibration curve (Y=aX+b) obtained from standard substance. Area under the curve ($AUC_{1h-24h}$) was calculated from the drug concentration in the serum, using WinNonlin (produced by the firm Pharsight, ver. 4.01). The results are as shown in Table 1 below.

TABLE 1

| test compound | $AUC_{1h-24h}$ (μg·h/ml) |
|---|---|
| compound 1 | 332 |
| compound 2 | 146 |
| compound 3 | 87 |
| compound 4 | 138 |
| compound 9 | 88 |
| compound A | 17 |
| compound B | 5 |
| compound C | 17 |
| compound D | 68 |

It turned out from the above test results that the compounds according to the present invention with methoxy or ethoxy at position 4 of benzimidazole ring exhibit apparently more excellent bioavailability than those of the known comparative compounds A, B, C and D with hydroxyl at position 4 of benzimidazole ring. Substantial increase in $AUC_{1h-24h}$ arises from the fact that the compounds of the present invention are greatly differentiated from the comparative compounds in profiles such as increase of maximum drug concentration ($C_{max}$) and extension of serum half-life (T1/2).

Test 2 (In Vivo Antitumor Test)

Human colon cancer WiDr was grown as subcutaneous tumor in mutant BALB/c nude mice. 2-mm-cube tumor fragments were transplanted subcutaneously into left flank of the nude mice. When the tumor reached logarithmic growth phase, mice were divided randomly into test groups consisting five mice per group. The samples prepared by dissolving test compound in dichloromethane with a ratio of the test compound to HPC(L) being 1:2.5, dried under reduced pressure and suspended in distilled water. The samples were then orally administered at a rate of test compound 100 mg/kg, once a day and six times a week in total, for two weeks. The length and width of the tumor mass were measured on a daily basis to calculate tumor volume. The tumor volume at each measured day was divided by that at the start day of the sample administration to calculate relative tumor growth rate; and the relative tumor growth rate of the treated groups (T) and that of the control group (C) were used to calculate T/C(%). Cases where T/C (%) of the last day was less than 50% and U-assay of Mann-Whitney revealed significant difference with one-sided risk rate of 1% were evaluated to be effective (+).

The results of typical compounds according to the present invention are as shown in Table 2 below.

TABLE 2

| test compound | T/C (%) | evaluation |
|---|---|---|
| compound 1 | 35.7 | + |
| compound 2 | 28.8 | + |
| compound A | 78.3 | − |
| compound B | 88.4 | − |

It turned out from the above test results that the compounds according to the present invention with methoxy at position 4 of benzimidazole ring are effective (+) and that the comparative compounds with hydroxyl at position 4 of the benzimidazole ring are ineffective (−).

It is apparent from Tests 1 and 2 that the compounds of the present invention exhibit remarkable improvement in pharmacokinetics. Such improvement resulted in excellent antitumor activities in vivo antitumor test. This was also supported by the results of Table 3 below showing test results of in vitro antitumor test (comparative tests in 50% growth inhibition concentrations ($GI_{50}$ μM) to Human colon cancer WiDr). Although in vitro antitumor test the compounds A and B exhibit more excellent effects than the compounds of the present invention, in the above-mentioned in vivo antitumor test the compounds of the present invention exhibit more intensive antitumor activities than those of the comparative compounds.

TABLE 3

| Test compound | $GI_{50}$(μM) |
|---|---|
| compound 1 | 0.45 |
| compound 2 | 0.14 |
| compound A | 0.15 |
| compound B | 0.09 |

The compounds of the present invention were also effective in vitro tests using human colon cancer cells, human lung cancer cells, human breast cancer cells or human prostata cancer cells and therefore positively expected is application of the compounds according to the present invention to treatment of various human solid cancers.

Next, description will be made on ways of administration, dosage forms and administered amount of the compounds of the present invention where they are applied to mammals, especially to human.

The compounds of the present invention may be administered orally or parenterally. In oral administration, the compounds may be in the dosage forms of tablets, coated tablets, powders, granules, capsules, microcapsules, syrups and the like; and in parenteral administration, in the form of injections which may include soluble freeze-dried forms, suppositories and the like. In the preparation of these forms, pharmaceutically acceptable excipients, binders, lubricants, disintegrants, suspending agents, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

The dosage for humans may depend on the condition of the disease to be treated, the age and weight of the patient and the like. A daily dosage for an adult may be in the range of from 50 to 500 mg and may be given once a day or in divided doses a day.

EFFECT OF THE INVENTION

The compounds according to the present invention exhibit remarkable improvement in pharmacokinetics, have by far more intensive antitumor activities with no aromatase inhibitory activities than conventional s-triazine and pyrimidine derivatives and are applicable to treatment of solid cancers.

BEST MODE FOR CARRYING OUT THE INVENTION

Next, the present invention is more specifically illustrated with reference to the following Examples of the compounds. It is to be, however, noted that the present invention is not limited to these Examples.

EXAMPLE 1

2-(2-difluoromethyl-4-methoxybenzimidazol-1-yl)-4-(cis-2,6-dimethylmorpholino)-6-morpholinopyrimidine (compound 1)

(1) To a solution of 2-difluoromethyl-4-methoxybenzimidazole (9.03 g, 45.6 mmol) in DMF (100 ml), 60% NaH (1.82 g, 45.6 mmol) was added and the reaction mixture was stirred for 30 minutes. Under the ice cooling, the reaction solution was added to a solution of 2,4,6-trichloropyrimidine (15.7 g, 92.1 mmol) in DMF (100 ml) and was stirred in ice bath for 30 minutes and further at room temperature for 2 hours. The reaction solution was poured into water and the precipitated crystals were collected by filtration and sufficiently washed successively with hexane and ether, and air-dried to obtain 12.3 g (yield: 78%) of 2-(2-difluoromethyl-4-methoxybenzimidazol-1-yl)-4,6-dichloropyrimidine.

(2) To the solution of the obtained 2-(2-difluoromethyl-4-methoxybenzimidazol-1-yl)-4,6-dichloropyrimidine (12.3 g, 35.7 mmol) in DMF (150 ml), cis-2,6-dimethylmorpholin (6.63 ml, 53.7 mmol) and potassium carbonate (7.35 g) was added successively at room temperature. The reaction solution was stirred at room temperature for 30 minutes and then was added with water and extracted with ethyl acetate for a few times. The organic layer was washed with saturated saline solution and dried over anhydrous magnesium sulfate. The solvent was removed under reduced pressure and the residue was sufficiently washed successively with hexane and ether, and air-dried to obtain 14.4 g (yield: 95%) of 4-chloro-2-(2-difluoromethyl-4-methoxybenzimidazol-1-yl)-6-(cis-2,6-dimethylmorpholino)pyrimidine.

(3) To the obtained 4-chloro-2-(2-difluoromethyl-4-methoxybenzimidazol-1-yl)-6-(cis-2,6-dimethylmorpholino)-pyrimidine (14.4 g, 34 mmol), morpholine (275 ml, 3.15 mol) was added and the mixture was stirred at room temperature for 30 minutes and further at 80° C. for 30 minutes. Water was added to the reaction solution and the precipitated crystals were collected by filtration, sufficiently washed successively with hexane, ether and ethyl acetate, and air-dried to obtain 13.7 g (yield: 86%) of 2-(2-difluoromethyl-4-methoxybenzimidazol-1-yl)-4-(cis-2,6-dimethylmorpholino)-6-morpholinopyrimidine.

Melting point: 132-134° C.

NMR ($CDCl_3$)δ: 1.28 (6H, d, J=6 Hz), 2.6-2.7 (2H, m), 3.6-3.9 (10H, m), 4.05 (3H, s), 4.1-4.2 (2H, m), 5.49 (1H, s), 6.79 (1H, d, J=8 Hz), 7.33 (1H, t, J=8 Hz), 7.42 (1H, t, J=54 Hz), 7.78 (1H, d, J=8 Hz)

MS m/z: 474($M^+$)

In accordance with the procedure of the Example 1, the following compounds were prepared from the corresponding starting materials.

2-(2-difluoromethyl-4-methoxybenzimidazol-1-yl)-4-(2,2-dimethylmorpholino)-6-morpholinopyrimidine (compound 2)

Melting point: 166-168° C.

NMR ($CDCl_3$)δ: 1.30 (6H, s), 3.49 (2H, s), 3.4-3.9 (12H, m), 4.05 (3H, s), 5.47 (1H, s), 6.79 (1H, d, J=8 Hz), 7.32 (1H, t, J=8 Hz), 7.41 (1H, t, J=54 Hz), 7.78 (1H, d, J=8 Hz)

MS m/z: 474($M^+$)

2-(2-difluoromethyl-4-methoxybenzimidazol-1-yl)-4-(cis-2,3-dimethylmorpholino)-6-morpholinopyrimidine (compound 3)

Melting point: 176-178° C.

NMR (CDCl$_3$)δ: 1.20 (3H, d, J=5 Hz), 1.22 (3H, d, J=5 Hz), 3.6-3.7 (1H, m), 3.6-4.1 (13H, m), 4.05 (3H, s), 5.47 (1H, s), 6.79 (1H, d, J=8 Hz), 7.32 (1H, t, J=8 Hz), 7.42 (1H, t, J=53 Hz), 7.78 (1H, d, J=8 Hz)

MS m/z: 474(M$^+$)

2-(2-difluoromethyl-4-methoxybenzimidazol-1-yl)-4-(trans-2,6-dimethylmorpholino)-6-morpholinopyrimidine (compound 4)

Melting point: 101-103° C.

NMR (CDCl$_3$)δ: 1.28 (6H, d, J=6 Hz), 3.3-4.2 (14H, m), 4.05 (3H, s), 5.46 (1H, s), 6.79 (1H, d, J=8 Hz), 7.32 (1H, t, J=8 Hz), 7.42 (1H, t, J=53 Hz), 7.78 (1H, d, J=8 Hz)

MS m/z: 474(M$^+$)

2-(2-difluoromethyl-4-methoxybenzimidazol-1-yl)-4,6-dimorpholinopyrimidine (compound 5)

Melting point: 203-205° C.

NMR (CDCl$_3$)δ: 3.6-3.9 (16H, m), 4.05 (3H, s), 5.50 (1H, s), 6.79 (1H, d, J=8 Hz), 7.32 (1H, t, J=8 Hz), 7.43 (1H, t, J=54 Hz), 7.78 (1H, d, J=8 Hz)

MS m/z: 446(M$^+$)

2-(2-difluoromethyl-4-methoxybenzimidazol-1-yl)-4-(cis-2,6-dimethylmorpholino)-6-morpholino-1,3,5-triazine (compound 6)

Melting point: 235-237° C.

NMR (CDCl$_3$)δ: 1.28 (6H, d, J=6 Hz), 3.56 (2H, s), 3.8-4.0 (12H, m), 4.05 (3H, s), 6.82 (1H, d, J=8 Hz), 7.34 (1H, t, J=8 Hz), 7.44 (1H, t, J=54 Hz), 7.86 (1H, d, J=8 Hz)

MS m/z: 475 (M$^+$)

2-(2-difluoromethyl-4-methoxybenzimidazol-1-yl)-4-(2,2,5,5-tetramethylmorpholino)-6-morpholino-1,3,5-triazine (compound 7)

Melting point: 209-211° C.

NMR (CDCl$_3$)δ: 1.57 (6H, s), 1.60 (6H, s), 2.6-2.8 (2H, m), 3.6-3.9 (8H, m), 4.05 (3H, s), 4.5-4.6 (2H, m), 6.81 (1H, d, J=8 Hz), 7.36 (1H, t, J=8 Hz), 7.47 (1H, t, J=54 Hz), 7.88 (1H, d, J=8 Hz)

MS m/z: 503(M$^+$)

2-(2-difluoromethyl-4-ethoxybenzimidazol-1-yl)-4,6-dimorpholinopyrimidine (compound 8)

Melting point: 188-190° C.

NMR (CDCl$_3$)δ: 1.56 (3H, t, J=7 Hz), 3.6-3.9 (16H, m), 4.32 (2H, q, J=7 Hz), 5.51 (1H, s), 6.79 (1H, d, J=8 Hz), 7.27 (1H, t, J=8 Hz), 7.42 (1H, t, J=54 Hz), 7.76 (1H, d, J=8 Hz)

MS m/z: 460(M$^+$)

2-(2-difluoromethyl-4-ethoxybenzimidazol-1-yl)-4-(2,2-dimethylmorpholino)-6-morpholinopyrimidine (compound 9)

Melting point: 114-116° C.

NMR (CDCl$_3$)δ: 1.30 (6H, s), 1.56 (3H, t, J=7 Hz), 3.49 (2H, s), 3.5-3.9 (12H, m), 4.32 (2H, q, J=7 Hz), 5.47 (1H, s), 6.78 (1H, d, J=8 Hz), 7.30 (1H, t, J=8 Hz), 7.41 (1H, t, J=53 Hz), 7.76 (1H, d, J=8 Hz)

MS m/z: 488(M$^+$)

Capability of Exploitation in Industry

Positively expected is application of the compounds of the present invention to treatment of various human solid cancers such as human colon cancer, human lung cancer, human breast cancer or human prostate cancer.

The invention claimed is:

1. A heterocyclic compound represented by the formula I:

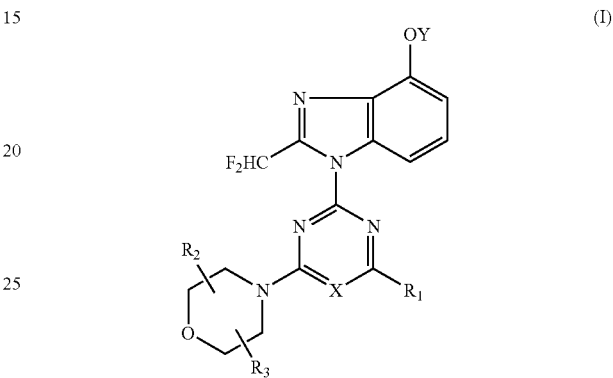

(I)

wherein

X represents nitrogen atom or CH;

Y represents $C_1$-$C_6$ alkyl;

$R_1$ represents morpholino (which may be substituted with one to four $C_1$-$C_6$ alkyl); and $R_2$ and $R_3$ each independently represent hydrogen atom or $C_1$-$C_6$ alkyl.

2. The compound of claim 1, wherein X is N.

3. The compound of claim 1, wherein X is CH.

4. The compound of claim 1, wherein Y is methyl.

5. The compound of claim 1, wherein Y is ethyl.

6. The compound of claim 1, wherein Y is n-propyl, iso-propyl, n-butyl, tert-butyl, n-pentyl or n-hexyl.

7. The compound of claim 1 wherein $R_1$ is morpholino that is not substituted.

8. The compound of claim 1 wherein $R_1$ is morpholino that is substituted with one to four $C_1$-$C_6$ alkyl groups.

9. The compound of claim 1, wherein $R_2$ and $R_3$ are each hydrogen.

10. The compound of claim 1, wherein only one of $R_2$ and $R_3$ is hydrogen.

11. The compound of claim 1, wherein $R_2$ and $R_3$ are each $C_1$-$C_6$ alkyl.

12. The compound of claim 1, wherein X is CH, Y is methyl, $R_1$ is morpholino, and $R_2$ and $R_3$ are each methyl.

13. The compound of claim 1 that is 2-(2-difluoromethyl-4-methoxybenzimidazol-1 -yl)-4-(cis-2,6-dimethylmorpholino)-6-morpholinopyrimidine.

14. The compound of claim 1 that is 2-(2-difluoromethyl-4-methoxybenzimidazol-1 -yl)-4-(2,2-dimethylmorpholino)-6-morpholinopyrimidine.

15. A composition comprising the compound of claim 1 and a pharmaceutically acceptable carrier, diluent, or excipient.

16. A method for inhibiting the growth of a human colon cancer cell, a human lung cancer cell, a human breast cancer cell, or a human prostate cancer cell comprising contacting the cancer cell with an effective amount of the compound of claim 1.

17. The method of claim 16, wherein said cancer cell is part of a solid human tumor.

18. The method of claim 17, wherein said contacting occurs in vivo.

* * * * *